United States Patent
Beavers et al.

(10) Patent No.: US 6,215,020 B1
(45) Date of Patent: Apr. 10, 2001

(54) BASIC CLAY CATALYST FOR THE PRODUCTION OF PENTYLGLYCOL MONOESTERS

(75) Inventors: William A. Beavers; Robert D. Culp, both of Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/343,215

(22) Filed: Jun. 30, 1999

Related U.S. Application Data

(60) Provisional application No. 60/091,173, filed on Jun. 30, 1998.

(51) Int. Cl.$^7$ .................................................. C07C 67/00
(52) U.S. Cl. ................................................. 560/238
(58) Field of Search ............................................. 560/238

(56) References Cited

U.S. PATENT DOCUMENTS

| | | |
|---|---|---|
| 2,879,298 | 3/1959 | Seligman ............................. 260/594 |
| 3,081,344 | 3/1963 | Hagemeyer, Jr. et al. .......... 260/494 |

(List continued on next page.)

FOREIGN PATENT DOCUMENTS

| | | |
|---|---|---|
| 391 674 | 10/1921 | (DE) . |
| 34 47 029 | 6/1986 | (DE) . |
| 0 284 397 | 9/1988 | (EP) . |
| 0 707 887 | 4/1996 | (EP) . |
| 870 204 | 3/1942 | (FR) . |
| 1 296 196 | 5/1962 | (FR) . |
| 308 285 | 3/1929 | (GB) . |
| 1 317 106 | 5/1973 | (GB) . |
| 77-15582 | 4/1977 | (JP) . |
| 58-65245 | 4/1983 | (JP) . |
| 92/01509 | 2/1992 | (WO) . |

OTHER PUBLICATIONS

Dartt et al., "Applications of Zeolites to Fine Chemicals Synthesis," Catalysis Today, 19:151–186, 1994.
Grim, R.E., *Applied Clay Mineralogy*, Chap. 2, McGraw–Hill Book Co., Inc., New York, 1962, 307–20.
Rode et al., "Aldol Condensation of Butanal over Alkali Metal Zeolites," Catalysis Letters, 9:103–114, 1991.
Tanabe, K., *Solid Acids and Bases, Their Catalytic Properties*, Chap. 4, pp. 73–80, Academic Press Inc., New York, 1970.
Velde, B., *Introduction to Clay Minerals—Chemistry, Origins, Uses and Environmental Significance*, pp. 164–172, Chapman & Hall, London, U.K., 1992.
Zhang et al., "Aldol Addition of Butyraldehyde over Solid Base Catalysts," Bull Chem Soc Jpn, 62(6):2070–2072, 1989.
Tsuji et al., "Self–Condensation of n–Butyraldehyde Over Solid Base Catalysts", *J. Catal.*, vol. 148, pp. 759–770 (1994).

Primary Examiner—Gary Geist
Assistant Examiner—Robert W. Deemie
(74) *Attorney, Agent, or Firm*—Rose M. Allen; Harry J. Gwinnell

(57) ABSTRACT

The invention is a base-modified clay that selectively catalyzes the formation of a glycol monoester from an aldehyde. The base-modified clay comprises a clay having secluded conjugate base sites and exchangeable interstitial cationic spaces. In the base-modified clay, the interstitial hydroxyl groups have been converted to oxide sites, at least one structural hydroxyl group has been converted to an oxide site. The base-modified clay contains sufficient conjugate base cations to balance the charge of said oxide groups. Processes for preparing the base-modified clay are described. The invention also provides a process for preparing a glycol monoester. This process includes heating in a reaction vessel an aldehyde and a catalytic amount of the base-modified clay under conditions sufficient to produce a glycol monoester.

7 Claims, 2 Drawing Sheets

U.S. PATENT DOCUMENTS

| | | | |
|---|---|---|---|
| 3,091,632 | 5/1963 | Hagemeyer, Jr. et al. | 260/476 |
| 3,291,821 | 12/1966 | Perry et al. | 260/494 |
| 3,718,689 | 2/1973 | McCain et al. | 260/494 |
| 3,876,706 | 4/1975 | Levanesky et al. | 260/602 |
| 4,163,757 | 8/1979 | D'Sidocky | 260/570 |
| 4,273,934 | 6/1981 | Merger et al. | 560/238 |
| 4,458,026 | 7/1984 | Reichle | 502/80 |
| 4,476,324 | 10/1984 | Reichle | 568/388 |
| 4,701,562 | 10/1987 | Olson | 568/390 |
| 4,704,478 | 11/1987 | Olson | 568/388 |
| 5,026,919 | 6/1991 | Dessau | 568/433 |
| 5,144,089 | 9/1992 | Arena et al. | 568/463 |
| 5,157,161 | 10/1992 | Knifton | 568/698 |
| 5,180,847 | 1/1993 | Thurman et al. | 560/238 |
| 5,254,743 | 10/1993 | Holmgren et al. | 568/463 |

BASIC CLAY CATALYST FOR THE PRODUCTION OF PENTYLGLYCOL MONOESTERS

RELATED APPLICATIONS

This application claims the benefit under 35 U.S.C. §119 to provisional application Ser. No. 60/091,173, filed Jun. 30, 1998, which is incorporated herein by reference in its entirety.

FIELD OF THE INVENTION

The invention relates to methods for the preparation of glycol monoesters from aldehydes using a base-modified clay as a catalyst. More particularly, the invention relates to base-modified clays that catalyze aldol condensations and Tischenko hydride shifts while minimizing side reactions such as transesterifications.

BACKGROUND OF THE INVENTION

Glycol monoesters are compounds having the following structure, where $R^1$ and $R^2$ are each either hydrogen or an organic group (e.g., an alkyl group):

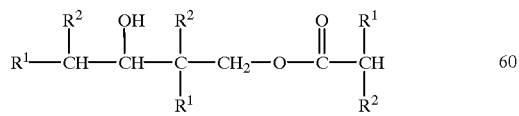

These compounds have a variety of uses. For example, glycol monoesters are used as industrial intermediates, solvents, plasticizers for polyvinylchloride and polyolefins, and coalescing aids for latex paints. One well-known glycol monoester is a product from 2-methyl propionaldehyde, where both $R^1$ and $R^2$ in the above formula are methyl groups, which is sold under the TEXANOL® trade name by Eastman Chemical Company, Kingsport, Tenn. The TEXANOL® product is the premier coalescing aid and leveling agent for latex paints and is also used as a plasticizer for polyvinylchloride products.

The formation of glycol monoesters from aldehydes is well known in the art. A typical process for forming glycol monoesters begins with an aldol condensation of an aldehyde having an alpha-hydrogen followed by a Tischenko hydride shift. Scheme I depicts these reactions, including the formation of a dioxanol intermediate.

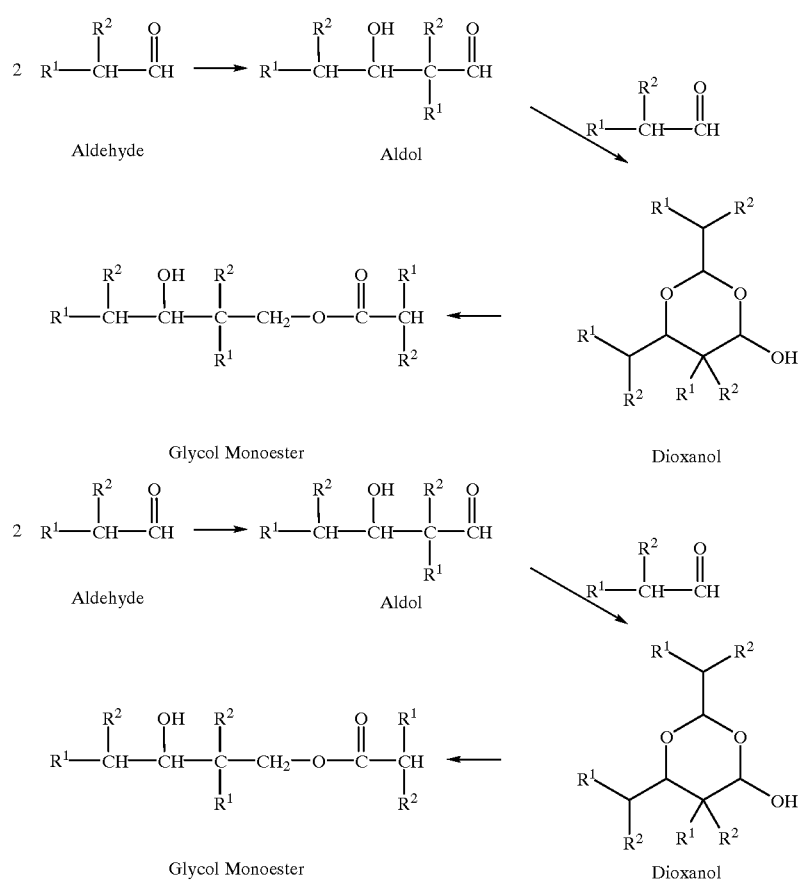

Although the glycol monoester above depicts the ester in the 1-position, the glycol monoester actually exists as a mixture of the 1- and 3-isomers. These isomers interconvert through an equilibrium (shown in scheme II) at sufficiently high temperature, in the presence of a catalyst, or over time.

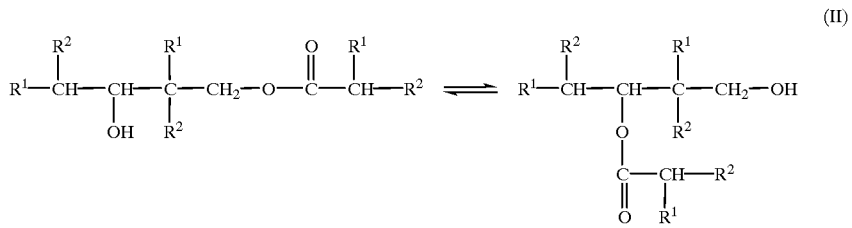
(II)

Under conditions used in most glycol monoester manufacturing processes, competing side reactions result in numerous undesirable by-products. Moderately high temperatures, for instance, favor transesterifications which yield glycol and glycol diester by-products. Simple ester by-products are believed to occur through either an intramolecular Tischenko reaction, (shown in scheme III), or through an intermolecular Cannizzarro reaction, (shown in scheme IV). High temperatures favor Cannizzarro reactions producing a simple ester by-product to the exclusion of the aldol condensation products. As a consequence of these unwanted by-products, the aldehyde conversion must be regulated to low to moderate levels to give optimum yields of glycol monoester. Even then, the desired glycol monoester yield rarely exceeds 85 to 90 percent without extensive recycling of the transesterification products.

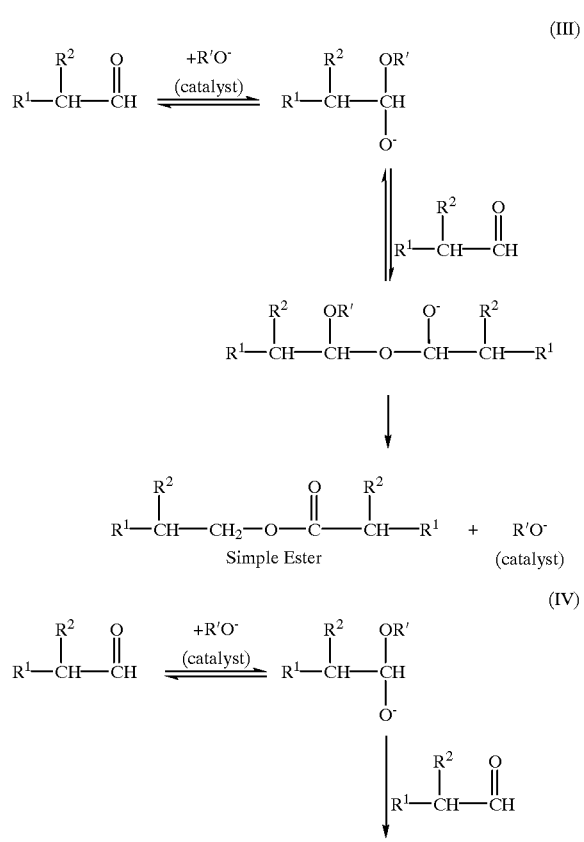

-continued

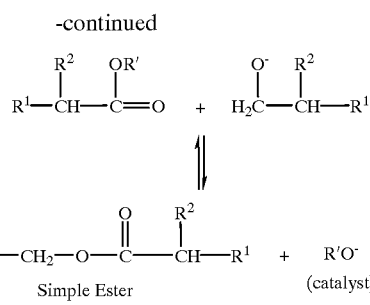

Strong bases have traditionally been used to promote the formation of glycol monoesters from aldehydes. For example, Hagemeyer et al., U.S. Pat. No. 3,081,344, describes how moderately basic aluminum alkoxides are good Tischenko catalysts, but poor aldol catalysts. Hagemeyer et al., U.S. Pat. No. 3,091,632, describes how highly basic sodium alkoxides are good aldol/Tischenko catalysts, but are poor Cannizzarro catalysts except at higher temperatures. The difference in catalytic base strength in these two patents accounts for the difference in the relative amounts of the simple ester product and the glycol monoester product. Both form from hemiacetals undergoing hydride attacks on carbonyl carbon atoms. The simple ester product forms from a hydride transfer from a hemiacetal of the starting aldehyde, and the glycol monoester forms from a hydride shift in the hemiacetal of the starting aldehyde and its aldol condensation product.

Additional by-products in the preparation of glycol monoesters are glycol, glycol diester and alcohol. These by-products result from transesterifications, as shown in schemes V–VII:

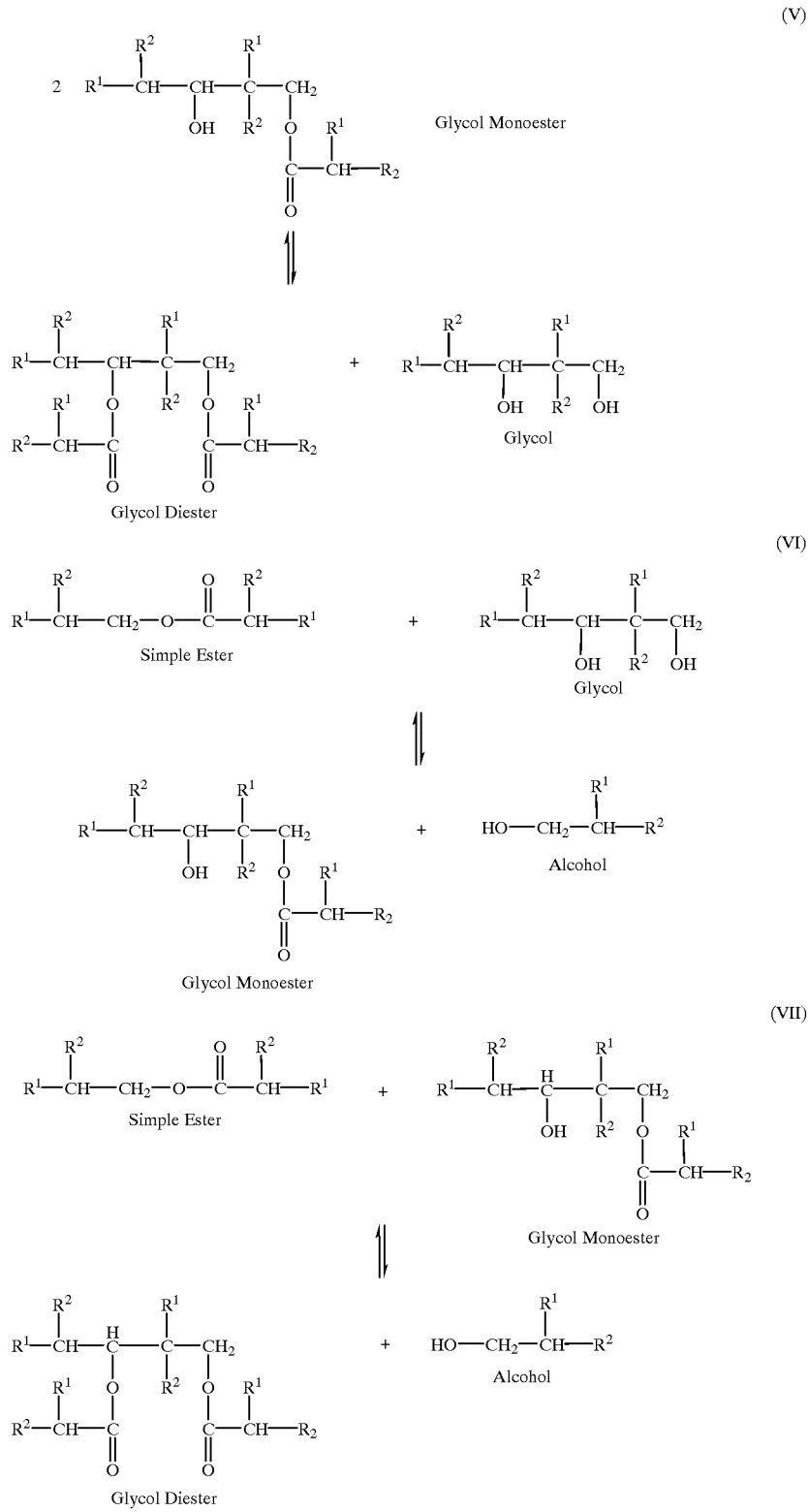

The extent of transesterification is generally related to the temperature and the reaction conditions for the aldehyde conversion. Under low simple ester production conditions, the limiting values of the transesterification keep the glycol:glycol monoester:glycol diester ratio near 1:2:1 so that the maximum yield of the glycol monoester is 50 percent. At high simple ester production conditions, the glycol:glycol monoester:glycol diester ratio becomes skewed toward the glycol diester as the simple ester transfers its ester group to the glycol derivatives releasing the alcohol. At high simple ester production conditions coupled with the limiting transesterification conditions, the yield of the glycol monoester may fall significantly below 50 percent. Even when the transesterification is not extensive, such as at low reaction temperatures and low aldehyde conversion rates, the yield of glycol monoester rarely exceeds 85–90 percent. The maximum yield of glycol monoester for the aqueous caustic system ranges from 75 percent, as shown by German Patent No. 3,447,029 to Weber et al. (1986), to 92 percent at moderate aldehyde conversions, as shown by Swedish Patent No. 468,559 to Hopfinger et al. (1993), to 98 at low aldehyde conversions percent, as shown by Japanese Patent No. 77 15,582 to Tsuchiya et al. (1977).

Because significant amounts of by-products often result, processes to prepare glycol monoesters require elaborate and costly purification schemes to separate the product from the by-products and to reconvert the by-products into glycol monoesters. Processes requiring over one dozen distillation columns and two or more reactors are not uncommon. Thus, a need exists for an improved glycol monoester synthesis. A further need exists for a catalyst that promotes aldol condensations and Tischenko hydride shifts to produce glycol monoesters while minimizing unwanted by-products.

SUMMARY OF THE INVENTION

In view of the industry's need for improved synthesis of glycol monoesters, the invention offers an improved process for their preparation. A base-modified clay of the invention catalyzes the reaction underlying this new process. Use of a base-modified clay according to the invention selectively catalyzes the reaction and advantageously minimizes, or even eliminates, unwanted by-products.

One embodiment of the invention is a base-modified clay that catalyzes the formation of a glycol monoester from an aldehyde. The base-modified clay has secluded conjugate base sites and exchangeable interstitial cationic spaces. Preferably, all interstitial hydroxyl groups of the clay have been converted to oxide sites, at least one structural hydroxyl group has been converted to an oxide site, and the clay contains sufficient conjugate base cations to balance the charge of said oxide groups.

Another embodiment is a process for preparing the base-modified clay. The process includes heating a clay in a basic solution under conditions sufficient to produce a clay having secluded conjugate base sites and exchangeable interstitial cationic spaces.

Yet another embodiment of the invention provides a process for preparing a glycol monoester. This process includes heating in a reaction vessel an aldehyde and a catalytic amount of a base-modified clay under conditions sufficient to produce a glycol monoester. The aldehyde has formula:

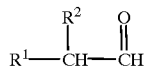

where $R^1$ and $R^2$ are independently selected from the group consisting of H, $C_{1-20}$ alkyl, $C_{2-20}$ alkenyl, $C_{2-20}$ alkynyl, $C_{3-20}$ cycloalkyl, and aryl; and the glycol monoester has a formula:

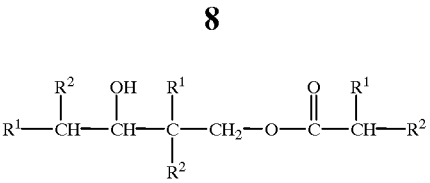

DETAILED DESCRIPTION OF THE INVENTION

Figure 1:
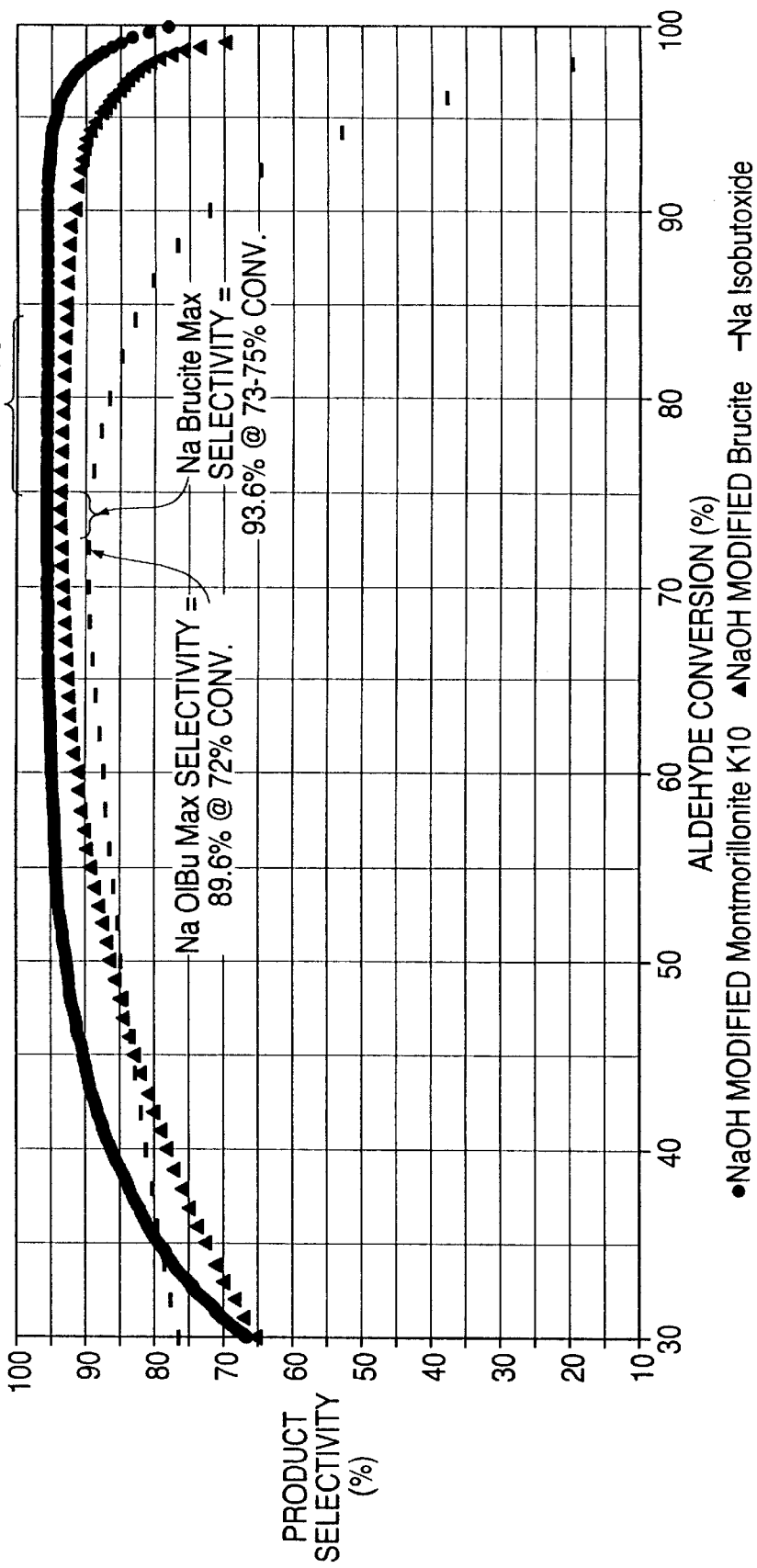
FIG. 1 depicts TMPD isobutyrate selectivity as a function of isobutyraldehyde for several catalysts.

According to the invention, a glycol monoester is prepared by a process using a base-modified clay to catalyze the conversion of an aldehyde having an alpha-hydrogen to a glycol monoester via an aldol condensation followed by a Tischenko hydride shift. This reaction is shown in scheme VIII:

(VIII)

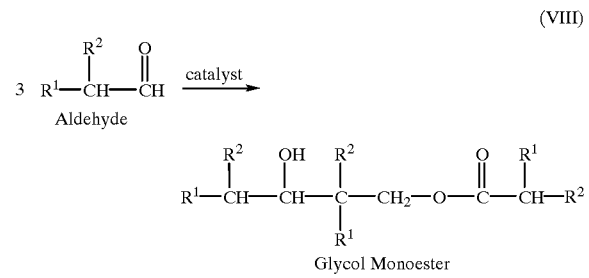

The Base-Modified Clays

In one embodiment, the invention relates to a base-modified clay having secluded conjugate base sites and exchangeable interstitial cationic spaces. Preferably, in the base-modified clay, all interstitial hydroxyl groups have been converted to oxide sites, at least one structural hydroxyl group has been converted to an oxide site, and the modified clay contains sufficient conjugate base cations to balance the charge of the oxide sites. In other words, the base-modified clay contains an actual number of sites per unit cell where an alkali metal or other base cation has been exchanged for the hydroxyl proton that exceeds a calculated number of exchangeable sites per unit cell in the unmodified clay.

Any clay having exchangeable hydroxyl sites may be used in this invention. The term "clays" encompasses not only clays, but also similar exchangeable minerals. Clays are generally microcrystalline, semi-microcrystalline, or amorphous mineral compounds of hydrated silicas and hydrated alumina, magnesias, iron oxides, and/or minor amounts of various other elements many of which exist as point impurities in the silica, alumina, magnesia, and/or iron oxide phases. Clays that are particularly useful in practicing the invention are the layered and exchangeable smectite clays, the partially exchangeable and hydrated illite clays, the hydrated chlorites, and other minerals with expandable and exchangeable interstitial cation spaces. These clays include, but are not limited to, montmorillonites, beidellites, nontronites, saponites, stevensites, sepiolite-palygorskites and hectorites, so-called degraded illites, hydrated chlorites, micas and other exchangeable and solvatable minerals including brucites, aluminas and silica gels.

Clays are typically acidic in their naturally occurring state. Because this acidity would catalyze undesirable side reactions, the clays of the invention are modified by treating them with a basic cation-containing solution. The acidic or basic character of a particular clay depends largely on the nature of the water of hydration. The water may exist as structurally bound hyrdoxyl groups (OH groups) as well as loosely bound $H_2O$. While intending not to be bound by any particular theory, it is believed that this base-modification serves two purposes. First, it neutralizes substantially all of the acid sites (OH sites) within the clay and replaces them with their conjugate basic sites (O). Second, the treatment impregnates or dopes the clay with cations from the base.

The base-modified clays of the invention can generally be characterized by the following properties. The crystalline fraction and the crystallographic structure, as shown by X-ray analysis, remains the same between the unmodified clay and the cation-doped clay. The ratios of the framework atoms, such as Si, Al, Mg, and Fe for the cation-doped clay remains substantially the same as the unmodified clay. However, the base cation is present in the base-modified clay in a concentration ranging from about 0.005 to about 20 weight percent, preferably from about 0.1 to about 15 weight percent, and even more preferably 0.5 to 10 percent weight. At low base concentrations, the catalyst activity remains low since the number of active sites is correspondingly small. At higher base concentrations, the clay acts more and more like a homogeneous base catalyst, and the catalyst selectivity for only primary aldol/Tischenko products diminishes.

It is believed that the cation present is in the form of chemically bound ions, not merely adsorbed, because they remain in the catalyst after repeated washings with solvent. While not desiring to be bound by any theory or scientific explanation, it is believed that the basified clays display unusual basic properties deriving from the location of the base within the highly inaccessible interior of the clay's layer structure and occurring in addition to typical base properties provided by base sites within the readily accessible interstitial cavity or at the clay's surface. It is believed that under the forcing conditions of the catalyst preparation, the unusual base properties form when the reagent base anions penetrate the interior of the clay's layer structure converting the sequestered acidic structural hydroxyl (OH) groups into their Bronstead conjugate base form, oxide (O—) groups. It is believed that the cationic counterions remain separate, largely within the interstitial cavity bound by ionic forces in order to balance charge but physically too large to fit into the clay's layer structure unless the outer shell of the clay layer is otherwise disrupted. It is believed that the resulting forced charge separation serves to further increase the basicity and further enhance the unusual basic properties. It is also believed that the number of basic sites, and thus the activity, and is directly proportionate to and therefore indicated by the amount of cation contained within the catalyst.

It is believed that lithium is an anomalous exception to basified clays described above due to its small size and propensity to form less ionic or covalent bonds. It is believed that the lithium cation may penetrate the clay's layer structure along with the base anion converting hydroxyl (OH) groups into tightly bound lithium oxide ion pairs, (OLi) groups, and displacing other ions especially in the octahedral layer sites. It is believed that this pervasive infusion explains why lithium loadings are often 2–4 times larger than other metal cations on a gram atom basis.

The base-modified clay contains sufficient metal cations to balance the charge of all oxide sites within the clay. Suitable metal cations include alkaline metals, such as the group 1 alkali metals, the group 2 alkaline earth metals, and various other metals, such as zinc, cesium, rubidium, and thallium. Preferred counterions are sodium, potassium and lithium. A base-modified clay may have a mixture of metal cations. A base-modified clay of the invention should have greater than or equal to 1.2 metal cations per unit cell. The number of metal cations per unit cell will vary depending on the metal used in the base-modification. The amount of metal cation in the clay can be readily determined by elemental analysis or other techniques known on the art. The amount of base-modification can be readily determined by comparing the elemental analysis of the starting clay and that of the base-modified clay. For example in the case of sodium, the concentration of metal cation in the base-modified clay should be greater than about 0.005 weight percent; more preferably, greater than about 0.1 weight percent; and most preferably, greater than 1 weight percent. Sodium-modified clays, for example, can have up to three or more sodium cations per unit cell giving a sodium concentration of 8 to 9 weight percent.

Lithium-modified clays have been found to have high concentrations of lithium cations. Lithium-modified clays have up to twelve lithium cations per unit cell. The lithium cation concentration may be as high as 10 weight percent in the base-modified clay. Preferably, the lithium cation concentration ranges from 0.1 to 15, and more preferably from 0.5 to 12.

Preferred base-modified clays of the invention not only have secluded conjugate base sites but also have cavities or spaces penetratable by the organic substrate adjacent to the base sites. To achieve these ends, the cavities preferably have a gallery width that is less than about 10.2 Å, as determined by the X-ray $d_{001}$ spacing and the clay layer width. More preferably, the gallery width ranges from about 9 Å to about 10.2 Å. It is also preferable that the cavities are wettable. Unwettable clays with neutral hydrophobic cavities, such as the talcs, or with highly charged cavities having tightly complexing counterions, such as the micas, are generally unsuitable.

The base-modified clay can be used in various forms to catalyze chemical reactions such as those described below. Accordingly, in another embodiment the invention relates to a catalyst composition comprising a base-modified clay as described above. For instance, the base-modified clay can be formed into granules, particles, pellets, spheres, tablets, rings, or extrudates and placed into a fixed bed reactor, as is known in the art. Preferably, the minimum dimension of the catalyst is greater than about 0.02 inches. In this variation of the invention, the reactants are passed over the catalyst bed and the crude product is collected at the other end. Alternatively, the catalyst can be stirred with the reactants as a slurry and the crude product separated from the catalyst by filtration, gravity settling, or centrifugation. In either case, the fact that the catalyst is a solid material and substantially insoluble in the reaction medium makes separation of the catalyst straightforward. It also avoids many costly environmental problems that are associated with the treatment and disposal of aqueous waste streams containing excess soluble base catalysts.

Preparation of Base-Modified Clays

Another embodiment of the invention is a process for preparing a base-modified clay. To prepare a base-modified clay of the invention, the clay is treated with a basic solution of a compound having a basic anion or an uncharged species capable of abstracting a proton from a hydroxyl group within the clay under conditions sufficient to produce a clay having secluded conjugate base sites and exchangeable interstitial cationic spaces. The species which extracts the hydroxyl group may, as explained below, be generated after the clay is treated with the compound. The solution may include either salts of a basic anion or other uncharged species in a solvent or as a neat liquid. As discussed above, the basic cation is preferably an alkaline metal cation from group 1 or 2 of the periodic table or other suitable metal cation. Suitable basic anions include, but are not limited to, hydroxide, amide, carbonate, silicate, metasilicate, phosphate, cyanide, borate, tetraborate, hydride, and aluminate. Suitable uncharged species include, but are not limited to, ammonia, amines, molten alkali metals, and alkali metal amalgams. Additional basic anions useful in the invention include other anions that are not intrinsically basic but that can be made basic with further treatment. Mixtures of basic compounds may be used in the base-modification to give a base-modified clay have a mixture of metal cations.

The solvent used in the preparation of the base-modified clays is not critical, provided its dielectric constant or complexing ability is high enough to serve as a solvent for both the entering basic moiety and the leaving cation and provided that it thoroughly wets the clay. Wetting is important for good base exchange. Suitable solvents include, but are not limited to, water, anhydrous ammonia, aqueous ammonia, and polar organic solvents such as ethers, alcohols, amines, ketones, dimethyl sulfoxide, and dimethyl formamide. Preferred solvents include liquid ammonia, dimethyl formamide and, more preferably, water.

One method of preparing a base-modified clay heats the clay, for example, with stirring, at reflux, and/or under pressure, in a basic solution for a sufficient amount of time to convert acidic hydroxyl (OH) sites, including interstitial and at least one structural hydroxyls, to oxide sites (O$^-$). As discussed, the oxide sites are the conjugate bases of the acidic hydroxyl sites. Preferably, the process includes heating, for example, with stirring, at reflux, and/or under pressure, a slurry of a clay in a basic solution for an amount of time sufficient to effect an exchange of a base for substantially all acidic sites on the surfaces of the clay. More preferably, the heating should continue until all interstitial hydroxyl groups of the clay have been converted to oxide sites and at least one structural hydroxyl group has been converted to an oxide site.

The reaction conditions for preparation of the base-modified clay are not critical. Generally, however, the temperature should be within the range of about 0° C. and about 500° C., preferably about 40° C. and about 120° C. Likewise, the reaction time is not critical, but generally ranges from about 0.5 h to about 100 h, preferably at least 6 h. If the heating time is too short, an insufficient of base-modification will take place. If it is too long, the clay may begin to decay or even decompose. The ratio of basic solution to clay should be greater than about 1:10 by weight. Preferably the ratio ranges from about 2:1 to about 100:1.

Typically, the conversion of acidic hydroxyl (OH) sites, including interstitial and at least one structural hydroxyls, to oxide sites (O$^-$) can be accomplished by heating, for example, with stirring, at reflux, and/or under pressure, for about 4 to 24 hours in a 5–50 percent preferably 10–30 percent aqueous solution of a Brönsted base. As long as the base is present in large excess, the actual concentration is not critical although lower concentration may require longer heating times. Heating times will vary depending on the particular clay and the number of hydroxyl groups to be converted. Preferably the base-modified clay may be prepared by heating the clay, for example, with stirring at reflux, and/or under pressure, for 6 to 12 hours in a 5–50 percent aqueous solution of an alkaline hydroxide, such as sodium hydroxide, lithium hydroxide, potassium hydroxide, magnesium hydroxide, calcium hydroxide and the like.

A base-modified clay of the invention may also be prepared by mixing the clay with a solution of a salt or other compound having an alkaline metal in combination with a species that undergoes combustion or pyrolysis to yield a basic species capable of extracting a proton from a hydroxyl group within the clay. A stoichiometric excess of the salt or other compound is first dissolved in an appropriate solvent and then mixed with the clay to treat the clay introducing the salt or other compound into the clay structure. The solvent is then removed or the clay isolated (e.g. by filtration) and the treated clay subjected to pyrolysis and/or combustion. Suitable salts and other compounds for this pyrolysis or combustion technique include, but are not limited to, carbonate, bicarbonate, nitrate, nitrite, azide, aliphatic and aromatic carboxylates, phenoxides, unsubstituted and substituted cyclopentadienes, and 1,3-carbonyl derivatives.

To illustrate, consider alkaline earth hydroxides, which have poor solubility in water. A soluble form of the cation can be dissolved in a solvent, intimately mixed with the clay, then the treated clay is subjected, for example, to pyrolysis or a combustion/pyrolysis process at 150° C. to 1250° C., thereby releasing small, neutral molecules which are often anhydrides of inorganic acids. The acid anhydrides then react with the hydroxyl sites in the clay affecting the desired base-modification. For example, a metal carbonate would decompose emitting carbon dioxide which, under oxidizing conditions, yields an oxide to extract the hydroxyl proton and, thereby, affecting the basic modification of the clay. Nitrates similarly decompose to an oxide under oxidative conditions. To affect this pyrolysis or combustion, the clay should be heated to a temperature less than its fusing temperature, avoiding a change in molecular structure of the clay. Preferred temperatures ranges from about 300° C. to 500° C., particularly for clays having a fusing temperature at or just above 600° C.

Preparation of Glycol Monoesters

Another embodiment of the invention is a process for preparing a glycol monoester by reacting at least one aldehyde in the presence of a base-modified clay. This process includes heating, for example, with stirring, at reflux, under pressure, in a reaction vessel the aldehyde(s) and the base-modified clay under conditions sufficient to produce a glycol monoester. The overall reaction of this process is shown in scheme VIII:

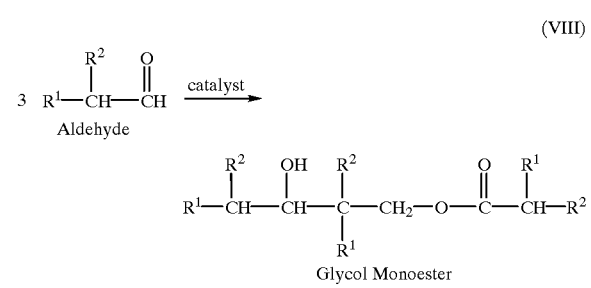

(VIII)

$R^1$ and $R^2$ is each independently selected from the group consisting of H, $C_{1-20}$alkyl, $C_{2-20}$alkenyl, $C_{2-20}$ alkynyl, $C_{3-20}$cycloalkyl, and aryl. Where $R_1$ or $R_2$ is an alkyl, alkenyl, alkynyl, cycloalkyl groups may be straight or branched, or unsubstituted or substituted. Preferred aldehydes are 2-alkylpropanals, 2-alkylbutanals, 2-alkylpentanals, and 2-alkylhexanals.

As many as three different aldehydes can be used to form a glycol monoester. Mixtures of more than one aldehyde will produce a mixture of glycol monoester products. Generally, it is more economically desirable to produce a single glycol monoester product. It is therefore preferred to prepare a glycol monoester according to the invention from only one aldehyde reactant.

Preferably, the at least one aldehyde is in the liquid phase and can be heated, for example, with stirring, at reflux, and/or under pressure with the base-modified clay catalyst. The aldehyde is present in an excess amount and acts as the solvent for the reaction, thereby obviating the need of a separate solvent. Depending upon the boiling point of the aldehyde, the temperature typically ranges from about 30° C. to 400° C., preferably from about 50° C. to 250° C. The temperature should not be so high as to degrade the starting aldehyde or the glycol monoester product.

It is also preferable to reflux the mixture in an inert atmosphere to prevent undesired reactions with the air. One of ordinary skill in the art would be able to use nitrogen, for example, to provide an inert atmosphere for the reaction. Advantageously, however, preparing a glycol monoester using a base-modified clay catalyst of the invention does not require the same rigorous inert conditions as needed with other syntheses.

The weight ratio of aldehyde to catalyst can range from about 1000:1 to 0.1 to 1, and preferably from 100:1 to 1:1. More preferably, the weight ratio is about 40:1.

The process of the invention typically affords the desired glycol monoester in yields exceeding 85% under normal aldehyde conversion ranging from 30 to 98+ %. Yields of 95% or greater can be achieved with aldehyde conversions of 50 to 98+ %.

If the aldehyde reactants are in poorly miscible or immiscible liquid phases, then an organic solvent may be used to make the phases of the reaction mixture miscible. Examples of such solvents include, but are not limited to, ethers, cyclic ethers, alcohols, amines, ketones, dimethyl sulfoxide, dimethyl formamide, or mixtures thereof. Preferably, the organic solvent is an ether of formula $R^6OR^7$, where $R^6$ and $R^7$ are selected from the group consisting of hydrocarbyl moieties having from 1 to 12 carbon atoms or together form a cycloalkyl or cycloalkenyl moiety having from 3 to 12 carbon atoms. Preferably, the organic solvent is tetrahydrofuran, tetrahydropyran, methanol, ethanol, propanal, isopropanal, or diethyl ether.

The organic solvent should preferably be added in a large enough amount that the reaction mixture remains homogeneous throughout the course of the reaction, yet small enough that the reactants are not diluted to the point of slowing down the reaction. Typically, the amount of organic solvent ranges from 0 to about 75% by weight. The preferred range for typical carbonyl-containing reactants is 5 to 50% by weight with 10 to 40% by weight being especially preferred.

The following discussion relates to what is believed to be the mechanism of catalysis for the production of glycol monoester and the competing side reactions. This discussion is intended merely to aid in the understanding of the invention not to limit it to any particular theory.

It is believed that the catalyst functions as a base in the same way that any base known in the prior art functions. The difference is that the base functionalities are sequestered in the catalyst cavities so that access to them is limited. Consequently, steric crowding in the rate determining transition state limits participation of that reaction to the final product mix. Likewise, the sequestering changes the nature of the base so that it forms covalent bonds poorly. In these cases, large spatial requirements for the transition state are disfavored as are species requiring covalent bonding to the base site.

The base site incorporated into the catalyst wall starts the Tischenko conversion by reversibly removing a proton from the dioxanol OH group. This dioxanalkoxide breaks down into an acyclic aldol hemiacetal conjugate base. Rotation of the H into the location formerly occupied by the $O^-$ sets the stage for the hydride shift to the carbonyl C. Pushed by the negative charge on the O and pulled by the HO conjugate acid site on the catalyst cavity wall, the hydride shift takes place irreversibly.

The size of this transition species depends on the size of the R groups. But in the case where R is methyl or some other primary alkyl group, the minimum diameter of the transition state is about 6.8 Angstrom units. Since the gallery width of montmorillonite is 9.6 Angstroms with no polar molecules in the cavity according to Grim, R. E., "Applied Clay Mineralogy," McGraw-Hill (1962), 307–20, there is enough room to accommodate this transition state and the reaction can physically take place. The spatial requirements of the intermediate dioxanol rearranging to form the glycol monoester is shown in Scheme IX:

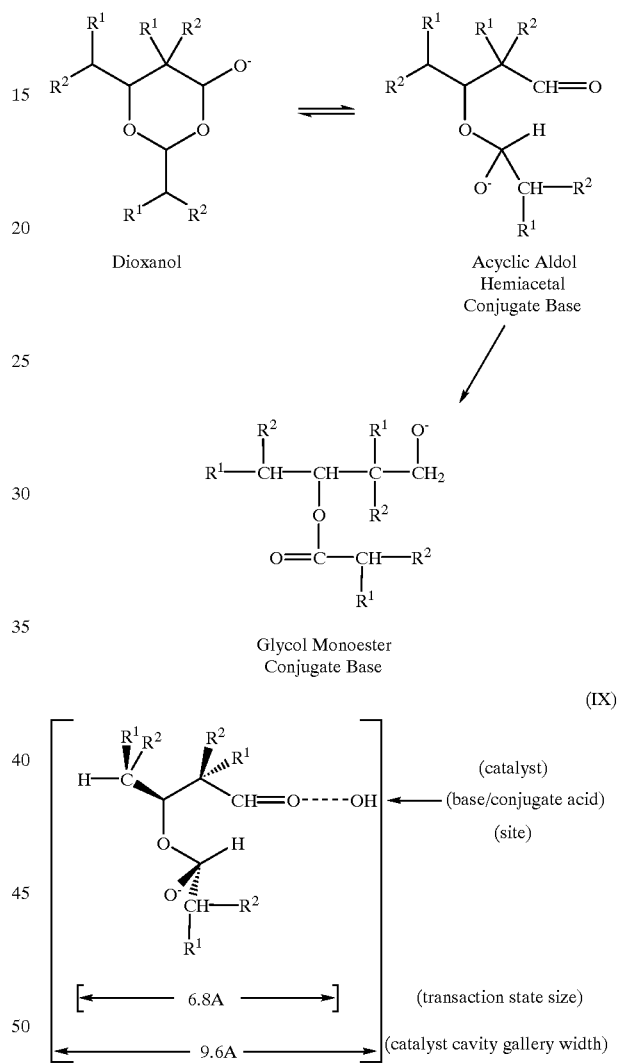

The transition state for the transesterification leading to the Glycol and the Glycol Diester crowds the bulky Glycol Monoester Conjugate base together with another bulky Glycol Monoester. There are almost twice as many atoms in this transition state as in the transition state leading to the Glycol Monoester itself. So as the configurations of the two species arrange themselves to minimize steric interactions, the spatial requirements grow. Most, but not all, of the arrangements expand into the unrestricted spaces.

In the one critical dimension cavity gallery width, the spatial requirement is about 10.2 Angstroms depending on what the R group is. Since the space available is only 9.6 Angstroms, the reaction cannot physically take place. Even though the active site might be capable of catalyzing this reaction, its action is blocked because the transition state will not fit into the available space. The spatial requirements for this transesterification are shown in Scheme X:

aldehyde carbonyl. This covalent bond formation is very difficult for the sequestered base sites in this catalyst, as

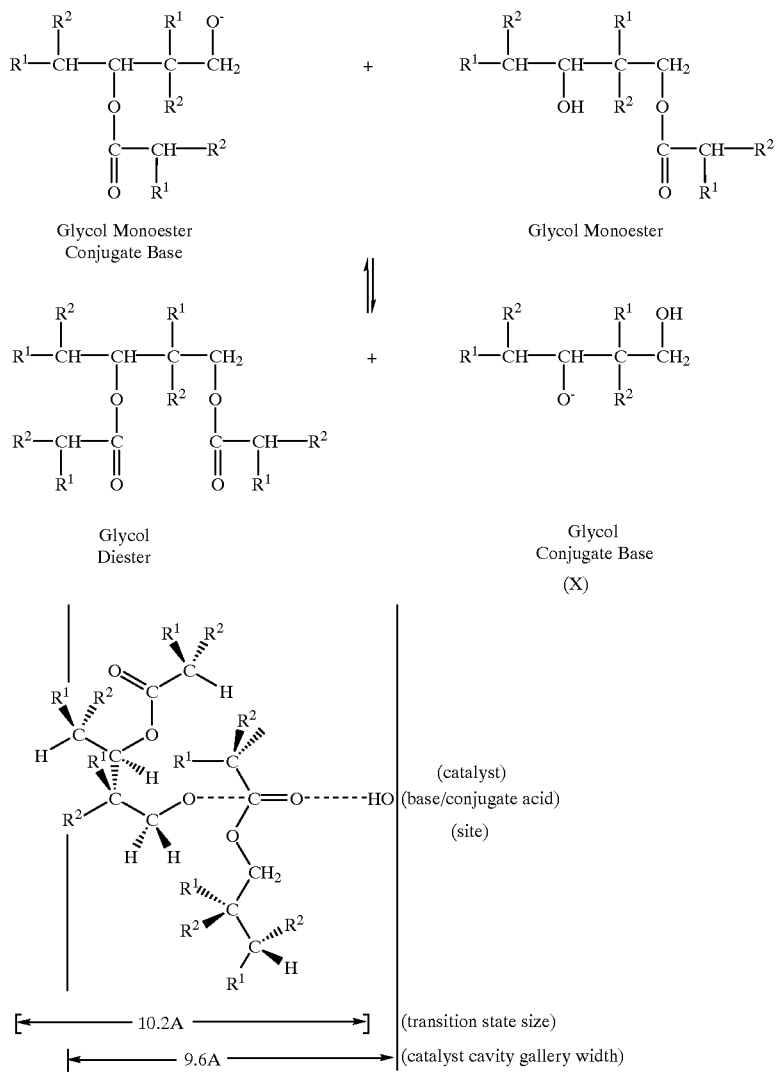

Under conditions in which the critical spacing expands due to the osmotic pressure exerted by a polar solvent or pillaring agent, the space constraints disappear. In this case the transesterification may take place; the high selectivity to glycol monoesters may decrease or disappear. Replacing the single product is a mixture of glycol monoester, glycol, and glycol diester. But returning the high selectivity is only a matter of replacing the solvent or pillaring agent causing the interstitial expansion so that the critical spacing returns to a more selective size.

The simple ester product forms by a Tischenko/Cannizzarro reaction. The transition state contains only two aldehyde units and is smaller than the transition state forming the glycol monoester. So size constraints for the transition state in the critical dimension are not important.

This reaction is limited by the nature of the basic sites in the catalyst. These sites are sequestered so they function as Brönstead but not Lewis bases. They can remove hydrogen ions due to their small size, but cannot easily react with larger groups due to steric constraints. As known from the prior art, the first step in the Tischenko/Cannizzarro reaction is an addition of the basic site in the catalyst to the C of the shown in Scheme XI:

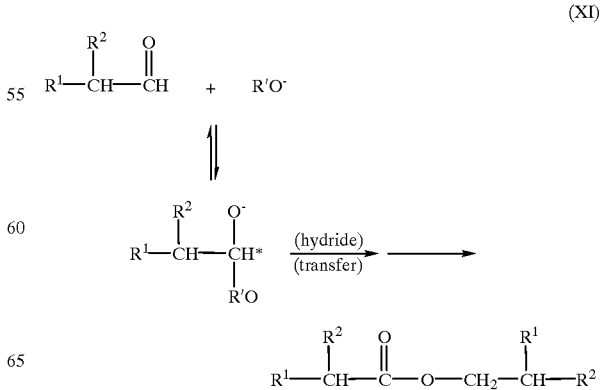

-continued

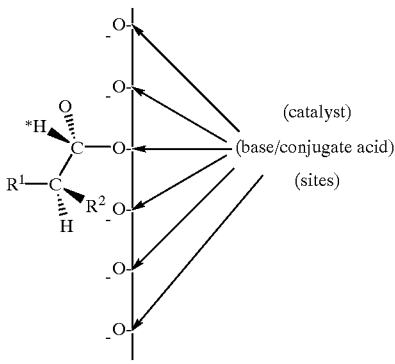

Even if this key intermediate were formed, it would react only if the carbonyl C of the attacking aldehyde could approach the hydride (*H—) in a reactive direction. The only reactive direction is parallel to the catalyst surface. So the same steric limits on the stability of this possible key intermediate would also limit the ability of an attacking aldehyde to participate in a Cannizzaro reaction.

EXAMPLES

The following examples are presented to illustrate, not limit, the disclosed invention. Although the invention is described in its preferred forms and with a certain degree of particularity, it is to be understood that changes can be made without departing from the spirit and scope of the invention. It is also to be understood that these examples do not define the limits under which the base-modified clay catalysts will perform.

Comparative Example 1

Reaction of 2-Methylpropanal with Untreated Clay Catalyst

The equipment for this experiment was a 500 milliliter round bottom flask equipped with a magnetic stirring bar, a thermowell to monitor the internal reaction temperature, and a reflux condenser topped with a nitrogen bubbler used to maintain a nitrogen blanket over the flask contents throughout the reaction. The charge to this equipment was 5.01 grams of powdered montmorillonite K10 clay and 250 milliliters of dry 2-methylpropanal (d=0.7869, 197 grams, 2.73 moles). Stirring the contents while heating to reflux for 200 hours caused the reaction temperature to increase from 65° C. to 82° C.

Analysis of the contents at that time showed a 90.6 percent conversion of the starting aldehyde into several dozen products. The yields of the aldol/Tischenko/Cannizzarro products were 3.2 percent Glycol Monoester (2,2,4-trimethyl-3-hydroxy-1-pentyl 2-methylpropanoate), 0.1 percent Glycol (2,2,4-trimethyl-1,3-pentanediol), 0.0 percent Glycol Diester (2,2,4-trimethyl-1,3-pentane di-(2-methylpropanoate)), 0.3 percent Simple Ester (2-methyl-1-propyl 2-methylpropanoate), and 0.3 percent Alcohol (2-methyl-1-propanol). The most abundant single product was 2,4,6-tri-(2-methylethyl)-1,3,5-trioxane in 15.8 percent yield.

Example 2

NaOH-Modification of Montmorillonite K10 Clay

The charge to a 1 liter round bottom flask equipped with an overhead stirrer and a reflux condenser was 200.3 grams of Montmorillonite K10 clay, 200 milliliters of 50 percent aqueous sodium hydroxide (d=1.5329, 153 grams NaOH, 3.83 moles), and 400 milliliters of water. Stirring and heating this mixture to reflux for 6 hours completed the base exchange. The workup consisted of a vacuum filtration of the mixture using a medium porosity glass frit funnel. Washing the filter residue with 3×150 milliliter portions of distilled water removed any residual caustic. Finally, air drying and oven drying at 300° C. for 4 hours completed the workup. The yield of the final material was 171.4 grams (85.6 percent).

The sodium content of the material also increased from 0.4 percent to 8.2 weight percent. Analysis of this material showed the critical $d_{001}$ interstitial spacing increased from 10 Å to 12 Å as a result of this exchange.

Example 3

Reaction of 2-Methylpropanal with NaOH-Modified K10 Clay Catalyst

This experiment used the equipment described in Example 1. The charge was 5.00 grams of the base-modified Montmorillonite K10 from Example 2 and 250 milliliters of dry 2-methylpropanal (d=0.7869, 197 grams, 2.73 moles). During 200 hours of stirring and heating to reflux, the reaction temperature climbed from 65° C. to 134° C.

Analysis of the product mixture showed a 94.5 percent conversion of the starting aldehyde. The reaction yielded 95.3 Glycol Monoester (2,2,4-trimethyl-3-hydroxy-1-pentyl 2-methylpropanoate). Other products included 0.3 percent Glycol (2,2,4-trimethyl-1,3-pentanediol), 0.3 percent Glycol Diester (2,2,4-trimethyl-1,3-pentane di-(2-methylpropanoate)), a trace (less than 0.1 percent) of Simple Ester (2-methylpropyl 2-methylpropanoate), 0.1 percent Alcohol (2-Methylpropanal), and 4.0 percent other materials.

FIG. 1 shows TMPD isobutyrate selectivity as a function of aldehyde conversion for isobutyraldehyde for several catalysts. As shown in FIG. 1, the NaOH-modified K10 clay catalyst produced greater selectivity over a greater range of aldehyde conversion.

Comparative Example 4

Reaction of 2-Methylpropanal with Sodium Isobutoxide Catalyst

This experiment demonstrated that the treated clay heterogeneous catalyst is superior to the best homogeneous catalyst at comparable 2-methylpropanal conversions. The equipment for this reaction was a one liter round bottom flask equipped with a magnetic stirring bar, a thermowell with thermometer, an addition funnel, and a reflux condenser topped with a nitrogen inlet connected to a bubbler. Flame drying all equipment under a stream of dry nitrogen and maintaining a dry nitrogen blanket throughout the reaction ensured its minimum exposure to water and air. The charge to this equipment was 500.0 milliliters of dry isobutyraldehyde (d=0.7869, 393.5 grams, 5.456 moles) in the round bottom flask and 25 milliliters of 1.0 M freshly prepared sodium isobutoxide in dry isobutyl alcohol. The assay of the isobutyraldehyde showed 15 ppm water and less than 100 ppm isobutyric acid.

The reaction began by heating the aldehyde to reflux while stirring and adding a few drops of the sodium isobutoxide catalyst. An increased reflux rate indicating the onset of the reaction began after the addition of 1.5 milliliters of the catalyst solution. Adding the catalyst drop by drop thereafter was necessary to control the vigorous reflux. It was necessary to wait at times up to 2 minutes between each added catalyst drop for the reflux rate to subside to ensure complete control of the reaction. After the addition of 3 milliliters of the catalyst solution, the flask contents solidified with the formation of the dioxanol. But continued catalyst addition soon redissolved this mass. The reaction continued until the temperature of the contents in the flask reached 132° C. The total added catalyst volume at this time was 11.3 milliliters (ca. 11 millimoles sodium isobutoxide) added over 2.2 hours. Analysis of this product mixture showed a 95.7 percent conversion of the starting aldehyde. The reaction yielded 58.2 percent Glycol Monoester (2,2,4-trimethyl-3-hydroxy-1-pentyl 2-methylpropanoate). Molar yields of other products included 16.7 percent Glycol (2,2,4-trimethyl-1,3-pentanediol), 16.0 percent Glycol Diester (2,2,4-trimethyl-1,3-pentan-di-(2-methylpropan-oate)), 5.8 percent Simple Ester (2-methylpropyl 2-methylpropanoate), and 3.3 percent other materials.

Figure 2:
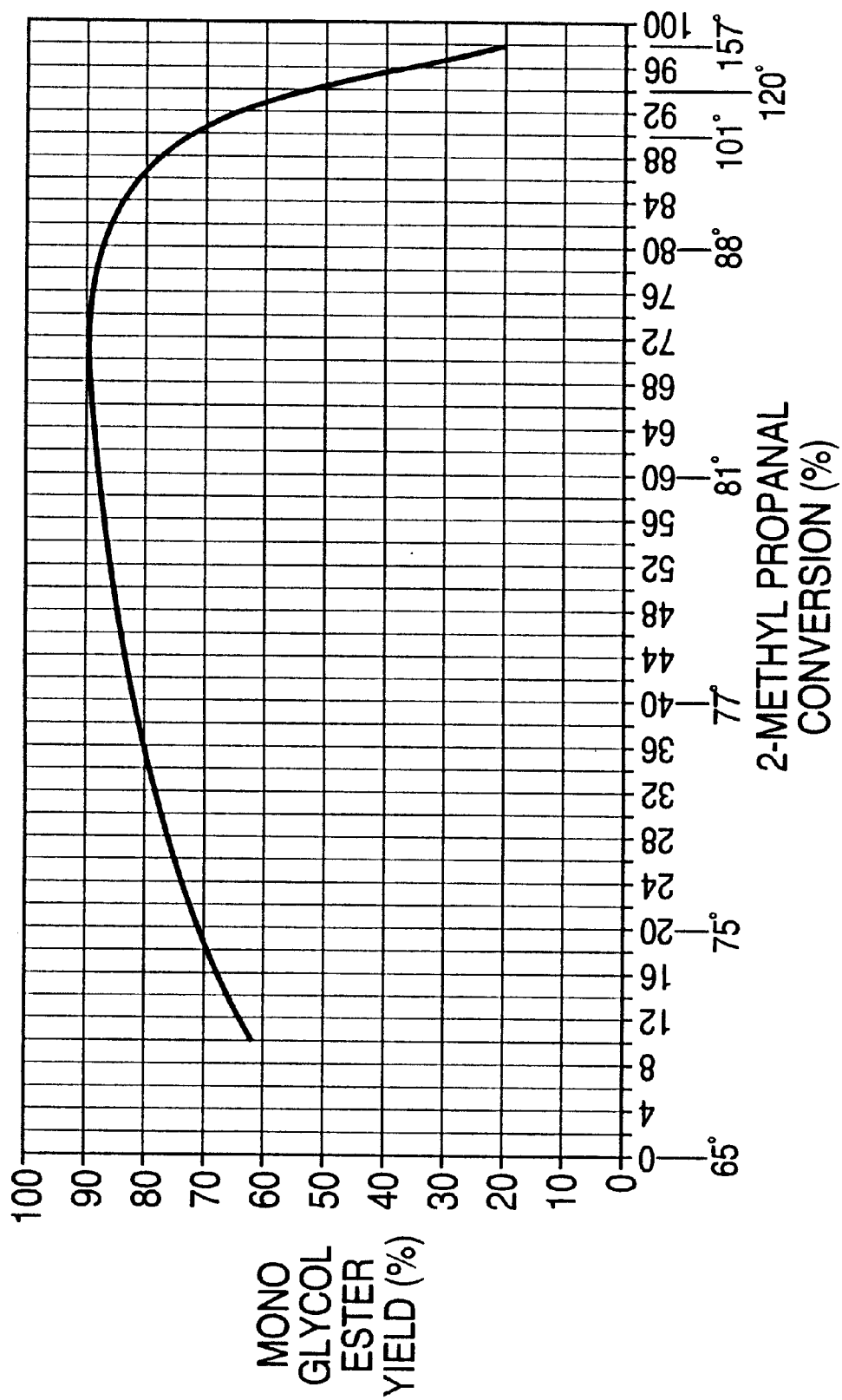
FIG. 2 depicts the monoester glycol yields for the reaction of 2-methyl propanal using a sodium isobutoxide catalyst.

FIG. 2 shows the main product yields for 2-methyl propanal as a function of conversion. Immediately below the conversion axis, the reflux temperatures corresponding to these conversions appear. As seen in FIG. 2, at no conversion does the yield of the aldol/Tischenko product (2,2,4trimethyl-3-hydroxy-1-pentyl 2-methylpropanoate) exceed 89 percent. And at some locations it falls below 25 percent. The factors limiting the yield of the aldol/Tischenko product are its transesterification into the diester and the glycol and the competing Cannizzarro reaction occurring before the aldehyde has undergone any aldol condensation. At high temperatures the Cannizzarro reaction is favored relative to the aldol condensation giving the Simple Ester rather than the Glycol Monoester product. At lower temperatures or with sufficiently basic catalysts, the free aldehyde shuttles through the aldol route (provided there is at least one alpha hydrogen) giving the Glycol Monoester instead of the Simple Ester.

Comparative Example 5

Reaction of 2-Methylpropanal with Calcium Oxide Catalyst

This experiment demonstrated that the base-modified clay heterogeneous catalyst is superior to typical heterogeneous catalysts. Experiment 3 was repeated using 5.02 grams of calcium oxide (89.5 millimoles) as the catalyst. After heating and stirring for 100 hours, the temperature had climbed from 65° C. to 98° C.

Analysis showed that the conversion of the 2-methylpropanal was 98.0 percent and the yield of Glycol Monoester was 66.0 percent. Molar yields of other products included 10.3 percent Glycol, 15.7 percent Glycol Diester, 0.8 percent Simple Ester, 0.3 percent Alcohol (2-methyl-1-propanol), and 6.9 percent other materials.

Comparative Example 6

Reaction of 2-Methylpropanal with NaY Zeolite Catalyst

This experiment demonstrated that the base-modified clay heterogeneous catalyst is superior to shape selective but inflexible heterogeneous catalysts. Experiment 3 was repeated using 5.00 grams of NaY zeolite as the catalyst. After heating and stirring for 400 hours, the temperature climbed from 65° C. to 135° C. Analysis showed that the conversion of 2-methylpropanal was 96.7 percent and that the yield of Glycol Monoester was 26.8 percent. Molar yields of other products included 8.8 percent Alcohol, 13.8 percent Simple Ester, 3.6 percent Glycol, 28.2 percent Glycol Diester, and 18.8 percent other materials.

Example 7

Reaction of 2-Methylbutanal with NaOH-Modified K10 Clay Catalyst

Experiment 3 was repeated using as the substrate 250 milliliters of 2-methylbutanal (d=0.8029, 201 grams, 2.33 moles). After heating and stirring for 150 hours, the reaction temperature had climbed from 92° C. to 157° C.

Analysis showed that the conversion of 2-methylbutanal was 93.4 percent and that the yield of Glycol Monoester (2,4-dimethyl-2-ethyl-3-hydroxy-1-hexyl 2-methylbutanoate) was 92.6 percent. Molar yields of other products included 1.7 percent Glycol (2,4-dimethyl-2-ethyl-1,3-hexanediol), 2.0 percent Glycol Diester (2,4-dimethyl-2-ethyl-1,3-hexanediyl di-(2-methylbutanoate)), 0.3 percent Simple Ester (2-methyl-1-butyl 2-methylbutanoate), 0.2 percent Alcohol (2-methyl-1-butanol), and 3.2 percent other materials.

Example 8

KOH-Modification of Montmorillonite K10 Clay

Example 2 was repeated using 100 grams of 85 percent potassium hydroxide in place of the caustic solution. All other conditions were the same. Starting with 200 grams of the Montmorillonite K10, the yield of the dried, treated product was 174 grams (87 percent). Elemental analysis showed a potassium content of 12.5 weight percent.

Example 9

Reaction of 2-Methylpropanal with KOH-Modified K10 Clay Catalyst

Experiment 3 was repeated using 5.01 grams of the potassium hydroxide modified Montmorillonite K10 from example 8 as the catalyst and 250 milliliters of dry (less than saturated with water) 2-methylpropanal (d=0.8029, 201 grams, 2.33 moles) as the substrate. After heating and stirring for 500 hours, the temperature climbed from 65° C. to 134° C.

Gas chromatographic analysis of the product at this point showed the conversion of 2-methylbutanal was 94.7 percent and the yield of Glycol Monoester was 91.9 percent. The yields of the other products were 3.6 percent Glycol Diester, 0.8 percent Glycol, 0.1 percent Simple Ester, 0.1 percent Alcohol, 0.6 percent glycol monoester precursors, and 2.7 percent other materials.

Example 10

LiOH-Modification of Montmorillonite K10 Clay

Example 2 was repeated using 100 grams of lithium hydroxide in place of the caustic solution. The water volume was also increased to 600 milliliters in this preparation. All other conditions were the same. Stating with 200 grams of the Montmorillonite K10 clay, the yield of the dried, treated product was 197 grams (98.5 percent). Elemental analysis showed a lithium content of 10.0 weight percent.

Example 11

Reaction of 2-Methylpropanal with LiOH-Modified K10 Clay Catalyst

Example 3 was repeated using 5.02 grams of the lithium hydroxide modified Montmorillonite K10 from example 10 as the catalyst and 250 milliliters of 2-methylbutanal (d=0.8029, 201 grams, 2.33 moles) as the substrate. After heating and stirring the reaction contents for 500 hours, the temperature in the reaction flask increased from 65° C. to 122° C.

Gas chromatographic analysis at this point showed the 2-methylpropanal conversion to be 96.9 percent and the yield of Glycol Monoesters to be 88.7 percent. The yields of the other components were 4.3 percent Glycol Diester, 0.5 percent Glycol, 0.1 percent Alcohol, 0.2 percent Simple Ester, 1.0 percent glycol ester precursors, and 5.2 percent miscellaneous materials.

Example 12

NaOH-Modification of Montmorillonite KSF Clay

Example 2 was repeated using 200 grams of Montmorillonite KSF in place of Montmorillonite K10. All other conditions were the same. Starting with 200 grams of the Montmorillonite KSF clay, the yield of the dried, treated product was 171.5 grams (85.8 percent). Elemental analysis showed a sodium content of 11.0 weight percent.

Example 13

Reaction of 2-Methylpropanal with NaOH-Modified KSF Clay Catalyst

Example 3 was repeated using 5.04 grams of the caustic modified Montmorillonite KSF clay from Example 12 as the catalyst. All other conditions were the same. After heating and stirring for 200 hours, the reaction temperature increased from 65° C. to 130° C.

Analysis showed the conversion of 2-methylpropanal to be 92.4 percent and the yield of Glycol monoester (GM) to be 92.2 percent. Molar yields of other products were 0.5 percent Glycol, 0.7 percent Glycol Diester, 0.5 percent Simple Ester, 0.5 percent Alcohol, and 5.6 percent other materials including precursors to the Glycol Ester.

A summary of the results of Examples 1, 3–7, 9, 11 and 13 are provided in Table I, below.

a 1"×24" stainless steel pipe containing a thermocouple to monitor the internal temperature and a pressure gauge to monitor the internal pressure. The catalyst pellets were loaded into this reactor and 4 separate reactions were run by pumping the substrate (2-methylpropanal) through the bed under a nitrogen pressure of 170 kPa. The process poremakers and results appear in Table II, below.

TABLE II

| Exp't No. | Temp (° C.) | Res Time (Hrs) | Conv (%) | Product Selectivities (%) | | | | | Prod Rate (#/ft³/hr) |
| | | | | Gly Monoester | Gly Diester | Gly | Simple Ester | Alc | |
| --- | --- | --- | --- | --- | --- | --- | --- | --- | --- |
| 1 | 104 | 3.9 | 30.7 | 95.5 | 0.3 | 0.7 | 0.2 | 0.1 | 3.8 |
| 2 | 129 | 3.8 | 35.6 | 93.0 | 0.6 | 1.0 | 0.4 | 0.3 | 4.4 |
| 3 | 152 | 3.0 | 36.8 | 91.4 | 1.5 | 0.8 | 0.4 | 0.4 | 5.7 |
| 4 | 181 | 2.0 | 25.7 | 88.4 | 3.5 | 0.6 | 0.5 | 0.5 | 5.8 |

Gly: glycol; Alc: alcohol

Example 15

LiOH-Modified Montmorillonite KSF Clay Preparation

A 1-Liter round bottom flask equipped with an overhead mechanical stirrer and a reflux condenser was charged with 201.3 grams of Montmorillonite KSF clay, 600 milliliters deionized water, and 152.7 grams of lithium hydroxide monohydrate (3.640 moles). This mixture was stirred and heated at reflux overnight. The slurry was then allowed to cool to room temperature. The solids were separated from the liquid by centrifugation. The liquid portion was decanted and discarded. The solids were washed by resuspending in 600 milliliters of deionized water and centrifuging. This sequence was repeated two more times to ensure removal of all soluble species. The catalyst was dried in an oven at 100° C. with flowing air for 24 hours. The yield of the final material was 214.2 grams.

TABLE I

| Example | aldehyde | catalyst | % to yield of GM | % conversion of aldehyde |
| --- | --- | --- | --- | --- |
| 1 | 2-methylpropanal | untreated K10 clay | 3.2 | 90.6 |
| 3 | 2-methylpropanal | NaOH-modified K10 clay | 95.3 | 94.5 |
| 4 | 2-methylpropanal | Sodium isobutoxide | 58.2 | 95.7 |
| 5 | 2-methylpropanal | Calcium oxide | 66.0 | 98.0 |
| 6 | 2-methylpropanal | NaY zeolite | 26.8 | 96.7 |
| 7 | 2-methylbutanal | NaOH-modified K10 clay | 92.6 | 93.4 |
| 9 | 2-methylpropanal | KOH-modified K10 clay | 91.9 | 94.7 |
| 11 | 2-methylpropanal | LiOH-modified K10 clay | 88.7 | 96.9 |
| 13 | 2-methylpropanal | NaOH-modified KSF clay | 92.2 | 92.4 |

Example 14

Bench Unit Operation

This experiment demonstrated the efficiency of the base-modified catalyst on continuous production of glycol monoesters. The base-modified Montmorillonite K10 catalyst from Example 2 was air dried and formed into 4–6 mesh pellets. Heating these pellets to 300° C. for 1 hour completed their preparation for bench unit operation. The reactor was X-ray diffraction analysis of this material exhibited the characteristic pattern for montmorillonite with a $d_{001}$ basal spacing of 10.2 Å, identical to the untreated montmorillonite KSF clay. The lithium content of the material increased from 0.004 weight percent Li to 9.3% by weight.

Example 16

LiOH-Modified Montmorillonite K10 Clay Preparation

Example 15 was repeated using 205.5 g of Montmorillonite K10 clay in place of the KSF type clay. All other conditions were essentially the same. The yield of the dried material was 209.7 g. X-ray diffraction analysis of this material exhibited the characteristic pattern for montmorillonite with a $d_{001}$ basal spacing of 10.2 Å, identical to the untreated montmorillonite K10 clay. The lithium content of the material increased from 0.002 weight percent Li to 9.0% by weight. This shows that different types of clay can be modified in the same manner.

The claimed invention is:

1. A process for preparing a glycol monoester comprising the step of heating in a reaction vessel a) an aldehyde having a formula $$R^1R^2CHO$$

where $R^1$ and $R^2$ are independently selected from the group consisting of H, $C_{1-20}$ alkyl, $C_{2-20}$ alkenyl, $C_{2-20}$ alkynyl, substituted or unsubstituted $C_{3-20}$ cycloalkyl, and aryl; and b) a catalytic amount of a base-modified clay, under conditions sufficient to produce a glycol monoester having a formula $$R^1R^2CHCH(OH)CR^1R^2CH_2O_2CCHR^1R^2.$$

2. A process of claim 1, where the base-modified clay has all interstitial hydroxyl groups converted to oxide sites, and at least one structural hydroxyl group has been converted to an oxide site, and the base-modified clay contains sufficient base cations to balance the charge of said oxide groups, and wherein the base-modified clay is derived from the group consisting of a montmorillonite clay, a beidellite clay, a nontronite clay, a saponite clay, a hectorite clay, a stevensite clay, a sepiolite-palygorskite clay, degraded illites, and hydrated chlorites; and the conjugate base cation is selected from the group consisting essentially of lithium, sodium, rubidium, cesium, and potassium.

3. A process of claim 1, wherein the weight ratio of aldehyde to base-modified clay is about 40:1.

4. A process of claim 1, wherein $R^1$ and $R^2$ are independently selected from the group consisting of H and $C_{1-10}$alkyl.

5. A process of claim 1, wherein the aldehyde is selected from the group consisting of 2-alkylpropanals, 2-alkylbutanals, 2-alkylpentanals, and 2-alkylhexanals.

6. A process of claim 1, wherein the step of heating is conducted in an inert atmosphere at a temperature ranging from about 50° C. to 250° C.

7. A process of claim 1, wherein the heating step is conducted in the presence of up to 75 weight percent of an organic solvent.

* * * * *